United States Patent [19]
Katayama et al.

[11] Patent Number: 5,663,322
[45] Date of Patent: Sep. 2, 1997

[54] DIADENOSINE TETRAPHOSPHATE TETRASODIUM SALT DODECAHYDRATE CRYSTALS AND PROCESS FOR PREPARATION

[75] Inventors: Tatsuo Katayama; Yoshihiro Nishikawa; Mayumi Hayashi; Hiroshi Nakajima, all of Kyoto; Masahiro Ozaki; Daiichi Watanabe, both of Tokyo, all of Japan

[73] Assignee: Unitika Ltd., Hyogo, Japan

[21] Appl. No.: 582,735

[22] Filed: Jan. 4, 1996

[30] Foreign Application Priority Data

Jan. 11, 1995 [JP] Japan ................................. 7-002951

[51] Int. Cl.$^6$ ............................................. C07H 19/20
[52] U.S. Cl. ............................ 536/26.22; 536/26.21
[58] Field of Search .......................... 536/26.21, 26.22; 514/47

[56] References Cited

U.S. PATENT DOCUMENTS 3,321,463  5/1967  Moffatt ........................... 536/26.22
4,886,749  12/1989  Dombou et al. ................. 435/89

FOREIGN PATENT DOCUMENTS 07242685  9/1995  Japan .

OTHER PUBLICATIONS

Reiss and Moffatt, "Dismutation Reactions of Nucleoside Polyphosphates. III. The Synthesis of α,ω–Dinucleoside 5'–Polyphosphates," *J. Organic Chem.*, 30, 3381–3387 (Oct. 1965).

*Biochemicals—Organic Compounds for Research and Diagnostic Reagents*, Catalog from Sigma Chemical Co., St. Louis, MO, 1992, p. 327, col. 2, entry No. D1262 (ammonium salt of 5'-Ado-p$_4$-5'-Ado).

Lüthje et al.(I), "Diadenosine Tetraphosphate (Ap$_3$A) Mediates Human Platelet Aggregation by Liberation of ADP," *Biochem. Biophys. Res. Comm.*, 118(3), 704–709 (1984).

Lüthje et al.(II), "Catabolism of Ap$_3$A and Ap$_4$A in Human Plasma—Purification and Characterization of a Glycoprotein Complex with 5'–Nucleotide Phosphodiesterase Activity," *Eur. J. Biochem.*, 149, 119–127 (1985).

Louie et al., "Diadenosine 5','''–P$^1$, P$^4$–Tetraphosphate, a Potential Antithrombotic Agent," *Thrombosis Res.*, 49, 557–565 (1988).

Primary Examiner—John Kight
Assistant Examiner—L. Eric Crane
Attorney, Agent, or Firm—Sughrue, Mion, Zinn, Macpeak & Seas

[57] ABSTRACT

The present invention is directed to diadenosine tetraphosphate (AP4A) tetrasodium salt dodecahydrate crystals represented by the following structure:

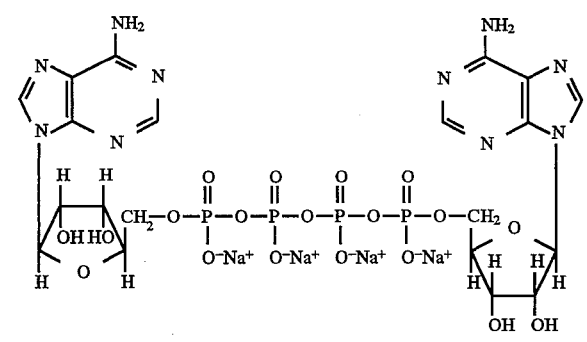

.12 H$_2$O

Compared with the conventional amorphous anhydride of AP4A tetrasodium salt, the AP4A tetrasodium salt dodecahydrate crystals of the present invention have a low hygroscopicity and very stable physical properties. During storage, they are scarcely affected by environmental humidity. Thus, the present crystals can be easily handled as a medicine or a starting material for preparing a medicine, which broadens their application range.

11 Claims, 3 Drawing Sheets

DIADENOSINE TETRAPHOSPHATE TETRASODIUM SALT DODECAHYDRATE CRYSTALS AND PROCESS FOR PREPARATION

FIELD OF THE INVENTION

This invention relates to diadenosine tetraphosphate tetrasodium salt dodecahydrate crystals. More particularly, it relates to diadenosine tetraphosphate tetrasodium salt dodecahydrate crystals which are useful as a medicine and a starting material for the production of a medicine because the crystals have various physiological functions.

BACKGROUND OF THE INVENTION

Diadenosine tetraphosphate (hereinafter sometimes referred to as AP4A) tetrasodium salt is a substance which is useful as a medicine and a starting material for the production of a medicine. AP4A tetrasodium salt has various physiological functions, such as promoting the synthesis of DNA on BHK cells suffering from $G_1$ inhibition (F. Grummt, *Proc. Natl. Acad. Sci.*, 75, p. 371, 1987), inhibiting phosphorylation (P. F. Maness et al., *J. Biol. Chem.*, 258, p. 4055, 1983) and inhibiting platelet aggregation (M. J. Harrison et al., *FEBS Letters*, 54, p. 57, 1975).

With respect to a method for producing AP4A, a method of freeze-drying AP4A as a sodium salt to thereby give AP4A as a solid product is known. Further, there has been known another method for producing AP4A tetrasodium salt by adding a hydrophilic organic solvent to an aqueous solution of AP4A tetrasodium (salt) in an amount of about fourfold of the aqueous solution and recovering the precipitate thus formed, to obtain the AP4A tetrasodium salt in the form of a solid powder.

However, the conventional AP4A tetrasodium salt, which is in the form of either a solid or a powder, is an amorphous anhydride and thus physically unstable. Moreover, it has an extremely high hygroscopicity. Due to these characteristics, it suffers from such problems as having poor storage stability, because it easily undergoes coloration, deliquescence, etc. In particular, if the coloration or deliquescence of solid or powdery AP4A tetrasodium salt occurs, it cannot be used as a medicine or a starting material for the production of a medicine. It is therefore required to strictly control the humidity, etc. of the storage environment. Accordingly, the conventional AP4A tetrasodium salt is disadvantageous for handling as a medicine or a starting material for the production of a medicine.

The present invention, which has been completed under these circumstances, aims at solving the above-mentioned problems accompanying the conventional solid or powdery AP4A tetrasodium salt by providing a novel AP4A tetrasodium salt which can be stored in a physically stable state and under a wide range of humidity conditions.

SUMMARY OF THE INVENTION

The present inventors have conducted extensive studies in order to solve the above-mentioned problems. As a result, they have successfully found that AP4A tetrasodium salt dodecahydrate crystals have a low hygroscopicity and extremely stable physical properties, thus completing the present invention.

Accordingly, the present invention provides diadenosine tetraphosphate tetrasodium salt dodecahydrate crystals represented by the following structure:

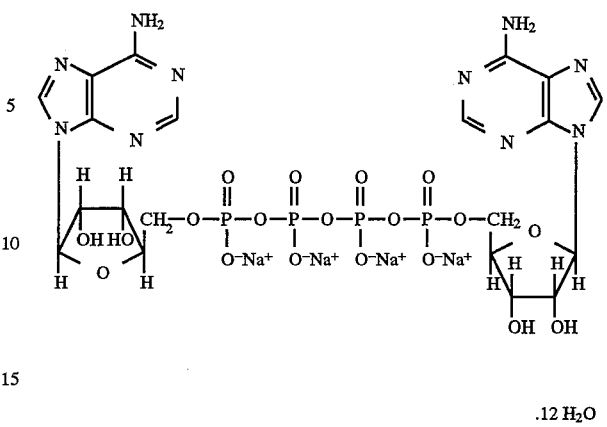

Compared with the conventional amorphous anhydride of AP4A tetrasodium salt, the AP4A tetrasodium dodecahydrate crystals of the present invention have an extremely low hygroscopicity (0 to 3%) and very stable physical properties with regard to the appearance (shape, color, etc.), moisture content (change in weight), and the like. Accordingly, they are scarcely affected by environmental humidity during storage. Thus, these crystals can be easily handled as a medicine or a starting material for preparing a medicine, which broadens the application range.

DETAILED DESCRIPTION OF THE INVENTION

Figure 1:
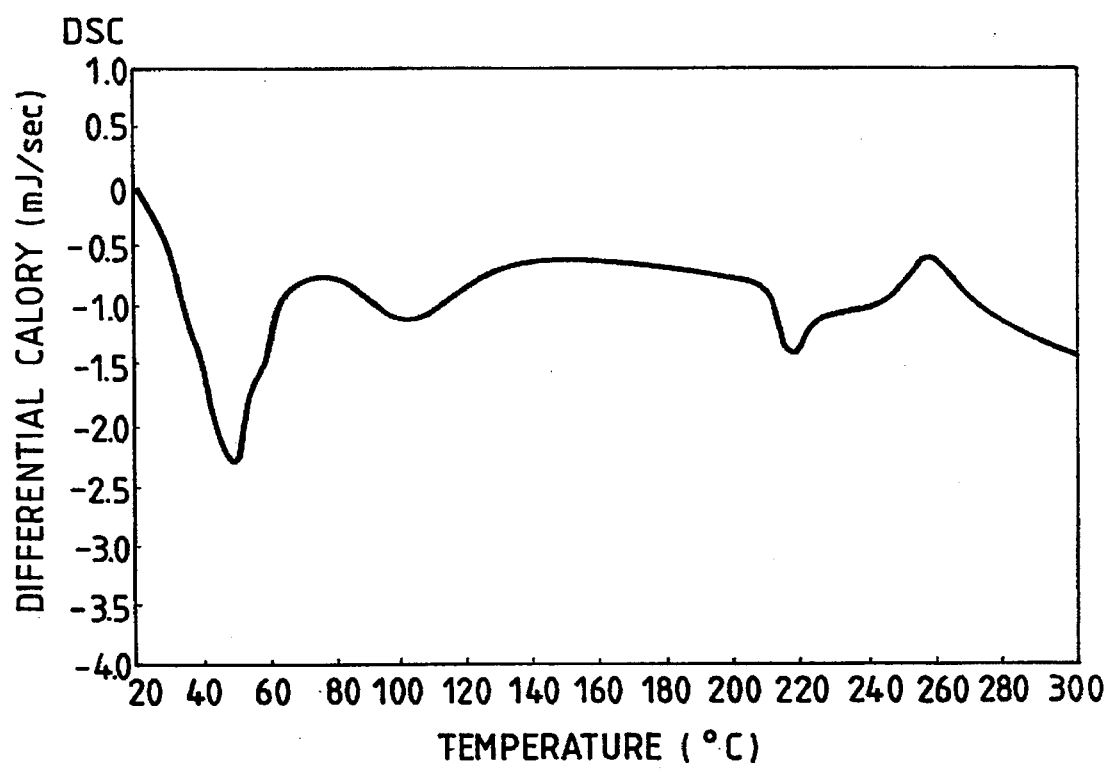
FIG. 1 shows the differential scanning calorimetric curve of the AP4A tetrasodium dodecahydrate crystals of the present invention.

The AP4A tetrasodium salt dodecahydrate crystals of the present invention can be produced by using AP4A as a starting material. This AP4A can be prepared by a known organic synthesis method starting from ATP or an enzymatic synthesis method with the use of an aminoacyl-tRNA synthetase (JP-B-5-73392 corresponding to U.S. Pat. No. 4,886, 749 (the term "JP-B" as used herein means an "examined Japanese patent publication")).

In the latter enzymatic synthesis method, for example, adenosine-5'-triphosphate or its derivative is reacted with an amino acid under the catalytic action of an aminoacyl-tRNA synthetase to thereby form diadenosine tetraphosphate or a derivative thereof. An arbitrary aminoacyl-tRNA synthetase may be used so long as it is capable of synthesizing dinucleoside tetraphosphate (NP4N). Particular examples thereof include lysyl-tRNA synthetase, histidyl-tRNA synthetase and phenylalanyl-tRNA synthetase originating in

*Escherichia coli*, lysyl-tRNA synthetase and phenylalanyl-tRNA synthetase originating in yeasts, phenylalanyl-tRNA synthetase originating in Fusarium, leucyl-tRNA synthetase originating in thermophilic bacteria such as *Bacillus stearothermophilus* and phenylalanyl-tRNA synthetase originating in sheep hepatic cells.

Examples of the amino acid which can be used in the reaction with adenosine-5'-triphosphate include α-amino acids such as tyrosine, alanine, leucine, isoleucine, phenylalanine, methionine, lysine, serine, valine, asparagine, aspartic acid, glycine, glutamine, glutamic acid, cysteine, threonine, tryptophan, histidine, proline and arginine. Each amino acid may be either an L-compound or a D-compound.

In the reaction between adenosine-5'-triphosphate with an amino acid, it is required to select an aminoacyl-tRNA synthetase specific to the amino acid employed. When leucine is employed as the amino acid, for example, then leucyl-tRNA synthetase is used.

After the completion of the reaction between adenosine-5'-triphosphate and an amino acid, the resulting reaction mixture contains unreacted AMP, ADP, ATP, etc. in addition to the reaction product (i.e., AP4A). It is therefore preferable to purify the reaction mixture by a known method with the use of, for example, an anion exchange resin (see, for example, *J. Org. Chem.*, 30, p. 3381–3387, 1965).

The purified reaction mixture thus obtained, which contains AP4A, contains sodium ions. Thus, AP4A is crystallized therefrom in the form of sodium salt crystals.

To crystallize the AP4A tetrasodium salt dodecahydrate crystals of the present invention from the above-mentioned purified solution containing AP4A, a hydrophilic organic solvent is added to the purified solution and then the crystals thus precipitated are collected by filtration and dried. The hydrophilic organic solvent employed for the crystallization can be a solvent which can be uniformly mixed with water, for example, alcohols such as methanol, ethanol and propanol, acetone, dioxane and acetonitrile. Any one of these solvents or a mixture of two or more may be used. It is necessary that the concentration of the hydrophilic organic solvent to be added is not more than 70% by volume based on the total volume after addition of the hydrophilic organic solvent. Preferably the concentration ranges from 20 to 60%, more preferably from 30 to 50% by volume based on the total volume after addition of the hydrophilic organic solvent. When the concentration of the hydrophilic organic solvent to be added to the solution exceeds 70% by volume based on the total volume after addition of the hydrophilic organis solvent, it is impossible to obtain the dodecahydrate crystals of the present invention.

Needless to say, a concentrated solution obtained by concentrating the purified solution containing AP4A can be used for the crystallization. The purified solution containing AP4A may preferably be an aqueous solution.

The solution containing the crystals thus precipitated is filtered and dried to thereby give the AP4A tetrasodium dodecahydrate crystals of the present invention. Filtration may be carried out by any methods such as gravity filtration, vacuum filtration, filtration under pressure, centrifugal filtration, squeezing filtration. The drying may be carried out by any means generally used in this field.

To further illustrate the present invention in greater detail, and not by way of limitation, the following Examples will be given. In these Examples, a water content was determined by the Karl Fischer method, unless otherwise noted. Unless otherwise indicated herein, all parts, percents, ratios and the like are by weight.

REFERENTIAL EXAMPLE 1

AP4A tetrasodium salt (1 g) was dissolved in 10 ml of water and then freeze-dried. Thus, 1 g of an amorphous anhydride of AP4A tetrasodium salt was obtained.

EXAMPLE 1

To 3.8 g of the amorphous anhydride of AP4A tetrasodium salt obtained in Referential Example 1 was added 25 ml of water. After dissolving the amorphous anhydride of AP4A tetrasodium salt, 20 ml of ethanol was further added and mixed. Then, the resulting mixture was allowed to stand at 5° C. for 3 days. The crystals thus precipitated were collected by filtration, washed with 1 ml of ethanol and dried. Thus, 1.57 g of AP4A tetrasodium dodecahydrate crystals were obtained.

The results of the elemental analysis of these dodecahydrate crystals are as follows.

Found (%): C 21.03; H 4.30; N 12.42; P 10.54 Calcd. (%): C 21.06; H 4.24; N 12.28; P 10.86 Optical rotation $[\alpha]^{20}_D$: −43.8° (in aqueous solution) Water content: 19.6% IR ($\gamma$KBr, cm$^{-1}$): 3400 to 3000, 1659, 1611, 1240, 894 (cm$^{-1}$) NMR ($\delta$, $D_2O$): 4.21–4.34 (4H, m), 4.37 (2H, m), 4.57 (2H, m), 4.72 (2H, m), 6.06 (2H, d, J=5.7 Hz), 8.13 (2H, s), 8.37 (2H, s)

Differential calorimetry:

A sample (2 mg) was subjected to differential calorimetry while elevating the temperature at a rate of 4.0° C./min. As FIG. 1 shows, apparent endothermic peaks were observed at 50° to 60° C., 90° to 110° C. and 220° to 230° C.

EXAMPLE 2

To 1 g of the amorphous anhydride of AP4A tetrasodium salt obtained in Referential Example 1 was added 6 ml of water. After dissolving the amorphous anhydride of AP4A tetrasodium salt, 4 ml of ethanol was further added and mixed. Then, 0.02 g of the seed crystals obtained in Example 1 were added and the resulting mixture was stirred for 20 hours. The crystals thus precipitated were collected by filtration, washed with 1 ml of ethanol and dried. Thus, 0.64 g of AP4A tetrasodium dodecahydrate crystals were obtained.

The water content of these dodecahydrate crystals was 19.6%.

EXAMPLE 3

To 1 g of the amorphous anhydride of AP4A tetrasodium salt obtained in Referential Example 1 was added 6 ml of water. After dissolving the amorphous anhydride of AP4A tetrasodium salt, 3 ml of methanol was further added and mixed. Then, 0.02 g of the seed crystals obtained in Example 1 were added and the resulting mixture was stirred for 20 hours. The crystals thus precipitated were collected by filtration, washed with 1 ml of methanol and dried. Thus, 0.37 g of AP4A tetrasodium dodecahydrate crystals were obtained.

The water content of these dodecahydrate crystals was 19.2%.

EXAMPLE 4

To 1 g of the amorphous anhydride of AP4A tetrasodium salt obtained in Referential Example 1 was added 6 ml of water. After dissolving the amorphous anhydride of AP4A tetrasodium salt, 4 ml of acetonitrile was further added and mixed. Then, 0.02 g of the seed crystals obtained in Example 1 were added and the resulting mixture was stirred for 20 hours. The crystals thus precipitated were collected by filtration, washed with 1 ml of acetonitrile and dried. Thus, 0.31 g of AP4A tetrasodium dodecahydrate crystals were obtained.

The water content of these dodecahydrate crystals was 19.0%.

EXAMPLE 5

To 1 g of the amorphous anhydride of AP4A tetrasodium salt obtained in Referential Example 1 was added 6 ml of water. After dissolving the amorphous anhydride of AP4A tetrasodium salt, 14 ml of 1-propanol was further added and mixed. Then, 0.02 g of the seed crystals obtained in Example 1 were added and the resulting mixture was stirred for 20 hours. The crystals thus precipitated were collected by filtration, washed with 1 ml of acetone and dried. Thus, 0.31 g of AP4A tetrasodium dodecahydrate crystals were obtained.

The water content of these dodecahydrate crystals was 19.7%.

EXAMPLE 6

A single crystal of the AP4A tetrasodium dodecahydrate of the present invention was subjected to X-ray crystal structure analysis. The data thus obtained including the atomic coordinates and isotropic temperature factors of atoms other than hydrogen are listed in Tables 1 to 3.

TABLE 1

| Atom | x | y | z | Beq |
|---|---|---|---|---|
| $P_1$ | 0.14712(7) | 0.0000 | 0.22767(10) | 2.00(2) |
| $P_2$ | 0.23227(7) | 0.12288(6) | 0.3481(1) | 2.07(2) |
| $P_3$ | 0.21982(7) | 0.22626(7) | 0.1196(1) | 2.15(2) |
| $P_4$ | 0.13221(7) | 0.34221(6) | 0.2672(1) | 2.10(2) |
| $Na_1$ | −0.3951(1) | −0.12699(9) | 0.2047(2) | 2.89(3) |
| $Na_2$ | 0.0962(1) | 0.17395(10) | 0.7395(2) | 3.07(3) |
| $Na_3$ | 0.3223(1) | 0.26031(9) | 0.4838(2) | 3.06(3) |
| $Na_4$ | −0.4030(1) | 0.47297(9) | 0.3021(2) | 3.02(3) |
| $O_1$ | −0.1660(2) | 0.0569(1) | 0.2924(3) | 2.79(6) |
| $O_2$ | −0.3697(2) | −0.0112(2) | 0.1716(4) | 3.53(6) |
| $O_3$ | −0.2147(2) | −0.1020(1) | 0.1227(3) | 2.48(5) |
| $O_4$ | 0.0240(2) | −0.0066(2) | 0.2074(3) | 2.94(6) |
| $O_5$ | 0.1575(2) | 0.0603(1) | 0.3494(3) | 2.62(6) |
| $O_6$ | 0.1867(2) | 0.0183(2) | 0.0720(3) | 3.16(6) |
| $O_7$ | 0.1913(2) | −0.0583(1) | 0.3099(3) | 2.81(6) |
| $O_8$ | 0.1759(2) | 0.1649(1) | 0.2139(3) | 2.80(6) |
| $O_9$ | 0.2216(2) | 0.1576(2) | 0.4997(3) | 3.09(6) |
| $O_{10}$ | 0.3394(2) | 0.1039(2) | 0.2999(4) | 3.41(6) |
| $O_{11}$ | 0.1300(2) | 0.2793(2) | 0.1534(4) | 3.68(7) |
| $O_{12}$ | 0.3195(2) | 0.2492(1) | 0.1926(3) | 2.77(6) |
| $O_{13}$ | 0.2168(2) | 0.2105(2) | −0.0487(3) | 3.88(7) |
| $O_{14}$ | 0.0107(2) | 0.3545(2) | 0.2914(3) | 3.22(6) |
| $O_{15}$ | 0.1736(2) | 0.3249(2) | 0.4233(3) | 3.53(7) |
| $O_{16}$ | 0.1806(2) | 0.3976(1) | 0.1816(3) | 2.70(6) |

TABLE 2

| Atom | x | y | z | Beq |
|---|---|---|---|---|
| $O_{17}$ | −0.1765(2) | 0.2854(1) | 0.2080(3) | 2.64(5) |
| $O_{18}$ | −0.3823(2) | 0.3484(2) | 0.3322(4) | 3.11(6) |
| $O_{19}$ | −0.2281(2) | 0.4425(1) | 0.3845(3) | 2.56(5) |
| $O_{20}$ | −0.3661(3) | −0.1217(2) | 0.4761(4) | 4.88(9) |
| $O_{21}$ | −0.5750(2) | −0.1096(2) | 0.2191(5) | 4.63(8) |
| $O_{22}$ | −0.4347(3) | −0.1540(2) | −0.0595(4) | 3.75(7) |
| $O_{23}$ | −0.3667(2) | −0.2475(2) | 0.2461(3) | 3.42(7) |
| $O_{24}$ | 0.0930(2) | 0.2908(2) | 0.7034(3) | 3.13(6) |
| $O_{25}$ | 0.1123(2) | 0.0574(2) | 0.7855(3) | 3.34(6) |

TABLE 2-continued

| Atom | x | y | z | Beq |
|---|---|---|---|---|
| $O_{26}$ | 0.4935(2) | 0.2332(2) | 0.3944(4) | 4.38(8) |
| $O_{27}$ | −0.3753(3) | 0.4770(3) | 0.0307(4) | 5.9(1) |
| $O_{28}$ | −0.3682(4) | 0.5942(2) | 0.2773(6) | 6.1(1) |
| $O_{29}$ | −0.4408(3) | 0.4968(2) | 0.5626(4) | 4.18(7) |
| $O_{30}$ | −0.5808(3) | 0.4556(2) | 0.2610(4) | 4.09(7) |
| $O_{31}$ | −0.5057(3) | 0.0891(2) | 0.0858(5) | 5.27(9) |
| $N_1$ | −0.3005(3) | 0.2792(2) | −0.1595(4) | 2.88(7) |
| $N_2$ | −0.3441(2) | 0.1843(2) | −0.0061(4) | 2.83(7) |
| $N_3$ | −0.0657(2) | 0.1796(2) | −0.0574(4) | 2.44(6) |
| $N_4$ | −0.1889(3) | 0.1224(2) | 0.0711(4) | 2.28(6) |
| $N_5$ | −0.1317(3) | 0.3077(2) | −0.2281(4) | 2.89(7) |
| $N_6$ | −0.2903(3) | 0.0604(2) | 0.5549(4) | 3.14(7) |
| $N_7$ | −0.3422(3) | 0.1548(2) | 0.5116(4) | 2.99(7) |
| $N_8$ | −0.0626(2) | 0.1625(2) | 0.5510(4) | 2.40(6) |
| $N_9$ | −0.1913(2) | 0.2184(2) | 0.4272(4) | 2.11(6) |

TABLE 3

| Atom | x | y | z | Beq |
|---|---|---|---|---|
| $N_{10}$ | −0.1195(3) | 0.0340(2) | 0.7246(4) | 2.78(7) |
| $C_1$ | −0.3056(3) | 0.2388(2) | −0.0853(5) | 3.14(9) |
| $C_2$ | −0.2403(3) | 0.1717(2) | −0.0079(4) | 2.03(7) |
| $C_3$ | −0.1642(3) | 0.2066(2) | −0.0856(4) | 2.16(7) |
| $C_4$ | −0.1965(3) | 0.2648(2) | −0.1605(4) | 2.13(7) |
| $C_5$ | −0.0835(3) | 0.1301(2) | 0.0367(4) | 2.36(7) |
| $C_6$ | −0.2397(3) | 0.0758(2) | 0.1767(4) | 2.54(7) |
| $C_7$ | −0.2787(3) | 0.0128(2) | 0.0961(4) | 2.29(7) |
| $C_8$ | −0.1883(3) | −0.0343(2) | 0.1297(4) | 2.16(7) |
| $C_9$ | −0.1516(3) | −0.0137(2) | 0.2937(4) | 2.33(7) |
| $C_{10}$ | −0.0409(3) | −0.0286(2) | 0.3347(4) | 2.75(8) |
| $C_{11}$ | −0.3597(3) | 0.0997(3) | 0.5925(6) | 3.75(10) |
| $C_{12}$ | −0.2375(3) | 0.1684(2) | 0.5100(4) | 1.99(7) |
| $C_{13}$ | −0.1586(3) | 0.1343(2) | 0.5840(4) | 2.07(7) |
| $C_{14}$ | −0.1872(3) | 0.0764(2) | 0.6597(4) | 2.21(7) |
| $C_{15}$ | −0.0856(3) | 0.2118(2) | 0.4571(4) | 2.42(8) |
| $C_{16}$ | −0.2463(3) | 0.2642(2) | 0.3233(4) | 2.23(7) |
| $C_{17}$ | −0.2879(3) | 0.3259(2) | 0.4061(4) | 2.32(7) |
| $C_{18}$ | −0.2000(3) | 0.3757(2) | 0.3740(4) | 2.05(7) |
| $C_{19}$ | −0.1675(3) | 0.3564(2) | 0.2085(4) | 2.20(7) |
| $C_{20}$ | −0.0571(3) | 0.3744(2) | 0.1652(5) | 2.68(8) |

Figure 2:
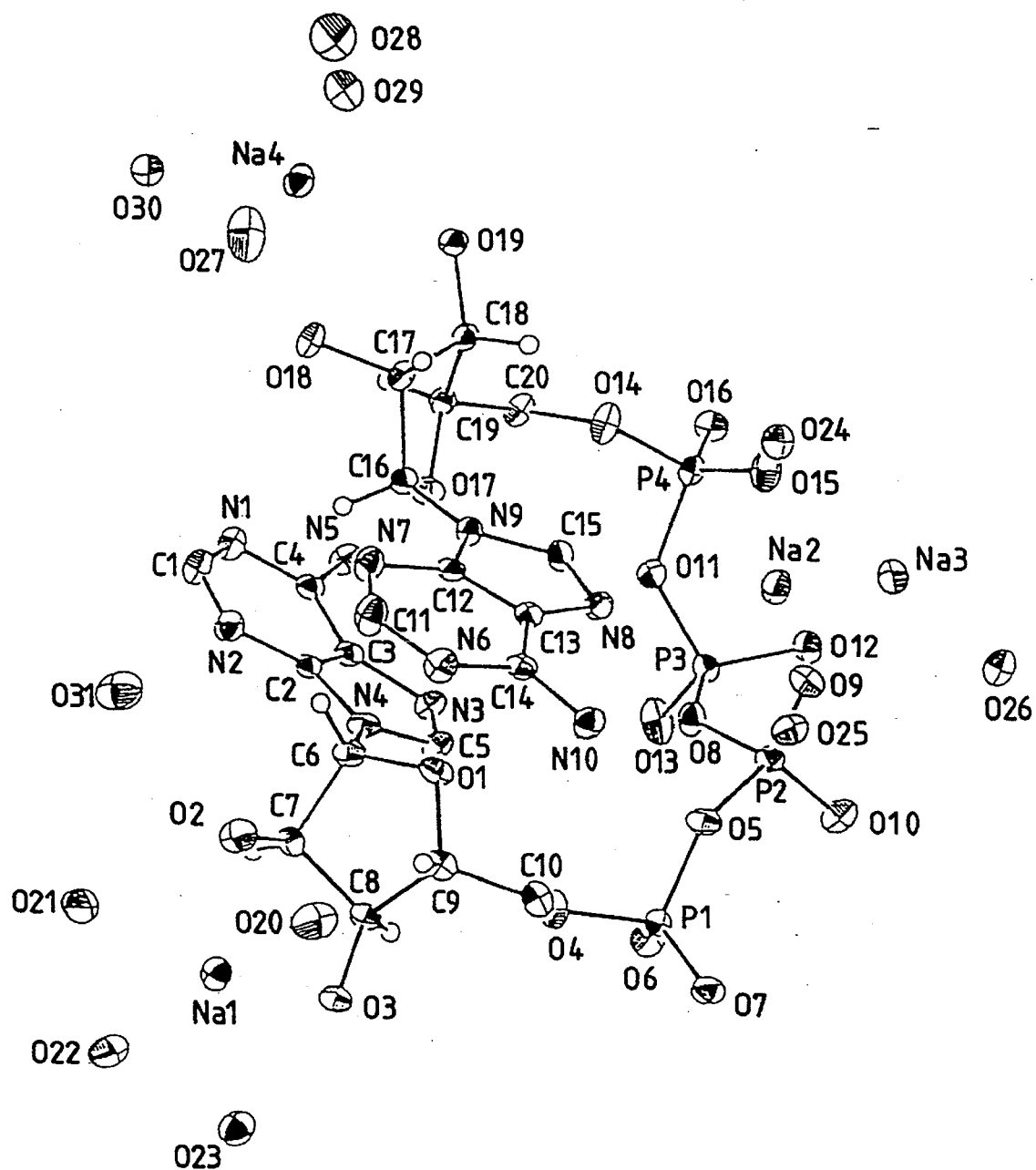
FIG. 2 shows the X-ray crystal structure analytical pattern which indicates a single AP4A tetrasodium dodecahydrate crystal of the present invention. The hydrogen atoms given in this figure are restricted to those binding to a chiral carbon atom.

These analytical results indicate that the AP4A tetrasodium dodecahydrate crystals of the present invention fall within the category of a monoclinic crystal system and involve one diadenosine tetraphosphate tetrasodium salt molecule and 12 water molecules per asymmetric unit. A unit cell is in a size of a=12.748 (2) Å, b=20.265 (3) Å, c=8.562 (2) Å and axial angle β=90.34 (1)°. The unit cell volume is V=2211.7 (6) Å$^3$, Z=2. The calculated crystal density is 1.712 g/cm$^3$ and the space group is P2$_1$. FIG. 2 shows the structure of the crystal.

EXAMPLE 7

The AP4A tetrasodium dodecahydrate crystals of the present invention were stored for 6 months under a relative humidity of 75% and at a temperature of 40° C. Then, the properties (appearance), optical rotation, purity, water content and content of AP4A tetrasodium salt were examined. The purity was determined by liquid chromatography (HPLC) and thin layer chromatography (TLC). The content was determined by the potentiometric titration method as will be described hereinbelow (cf. *Daijuichikaisei Nihonyakyokuho Kaisetsusho* (Explanation of Japanese Pharmacopeia, 11th revision), Hirokawa Shoten). Namely, 500 mg of the sample was precisely weighed and dissolved in 50 ml of water. Then, 0.05N hydrochloric acid for volumetric analysis was dropped thereinto and the potential difference was measured. The results were plotted and thus the end point was determined from the plot. The water content of the sample was determined by the Karl Fischer method and thus the content of the AP4A tetrasodium salt was corrected (in terms of anhydride). One milliliter of the 0.05N hydrochloric acid corresponds to 23.108 mg of anhydrous AP4A tetrasodium salt.

Table 4 shows the results of the measurements.

TABLE 4

| Measurement item | Measurement time | |
|---|---|---|
| | Starting | After 6 months |
| property/appearance | white crystalline powder | no change |
| specific rotation $[\alpha]^{20}_D$ (°) | −44.0 | −43.6 |
| purity: | | |
| HPLC (%) | 0.13 | 0.20 |
| TLC 1 | 1 spot | 1 spot |
| TLC 2 | 1 spot | 1 spot |
| water content (%) | 19.7 | 19.3 |
| content: potentiometric titration (%) | 100.1 | 99.5 |

TEST EXAMPLE 1

Figure 3:
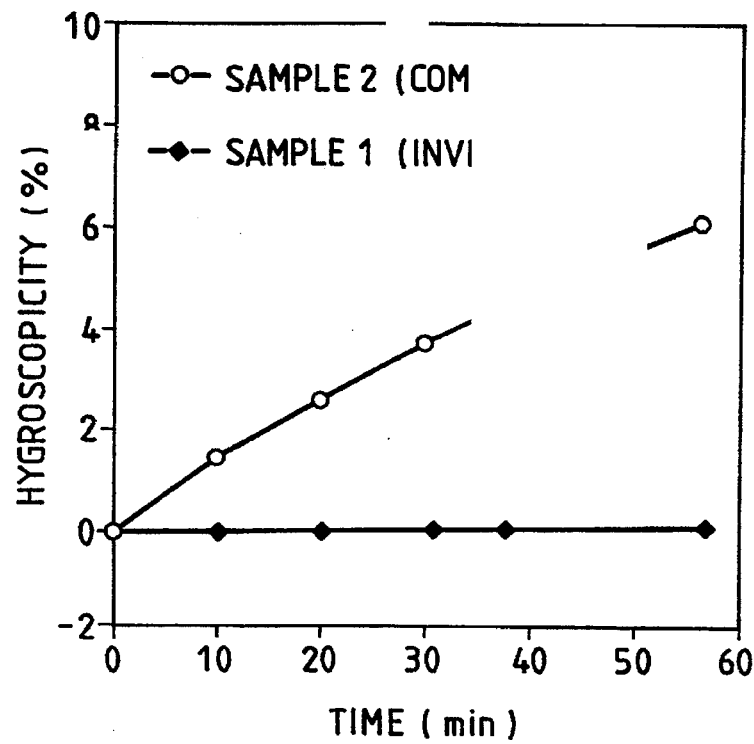
FIG. 3 shows changes in the hygroscopicity of the AP4A tetrasodium dodecahydrate crystals of the present invention and that of a known amorphous anhydride of AP4A tetrasodium salt with the passage of time.

The AP4A tetrasodium dodecahydrate crystals of the present invention (sample 1) and the amorphous anhydride of AP4A tetrasodium salt (sample 2) employed for comparison were allowed to stand under a relative humidity of 63% and at a temperature of 23° C. and changes in weight due to water absorption were monitored. FIG. 3 shows the results. Thus, it was proved that the hygroscopicity of the dodecahydrate crystals of the present invention was lower than that of the comparative sample.

TEST EXAMPLE 2

Figure 4:
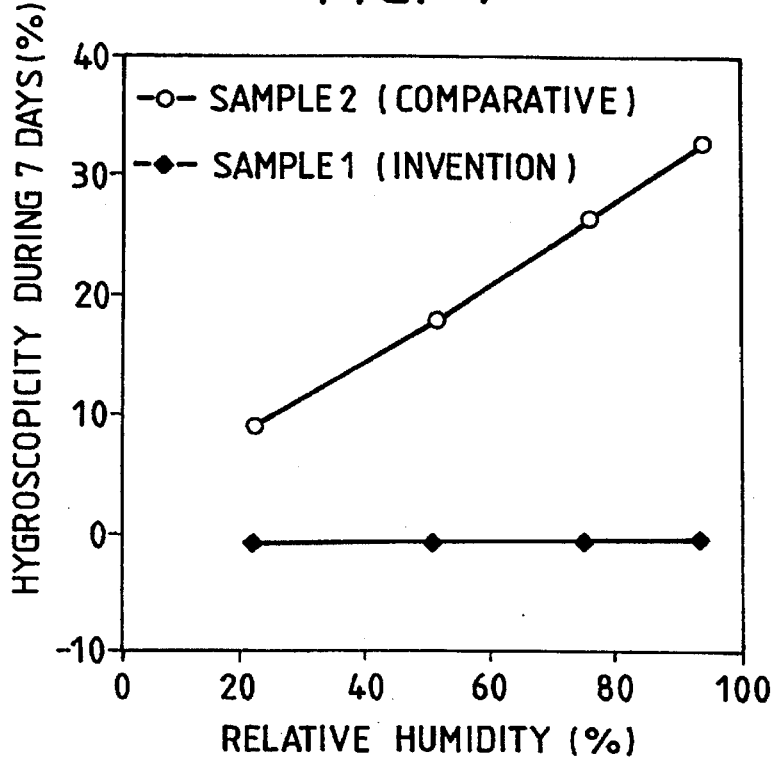
FIG. 4 shows changes in the hygroscopicity of the AP4A tetrasodium dodecahydrate crystals of the present invention and that of a known amorphous anhydride of AP4A tetrasodium salt over a period of 7 days.

The same samples 1 and 2 as those employed in Test Example 1 were allowed to stand for 7 days under relative humidities of 22%, 51%, 75% and 93% and at a temperature of 25° C. and changes in weight due to water absorption were monitored. FIG. 4 shows the results. Thus, it was proved that the hygroscopicity of the dodecahydrate crystals of the present invention was lower than that of the comparative sample at every relative humidity tested.

TEST EXAMPLE 3

The same samples 1 and 2 as those employed in Test Example 1 were allowed to stand for 7 days under a relative humidity of 60% and at a temperature of 30° C., or under a relative humidity of 75% and at a temperature of 40° C., and changes in properties (appearance) and changes in weight due to water absorption were monitored. Table 5 shows the results. Thus, it was proved that the dodecahydrate crystals of the present invention showed a lower hygroscopicity and more stable properties than those of the comparative sample at every condition tested.

TABLE 5

| Storage condition | Temperature: 30° C. Relative Humidity: 60% | | Temperature: 40° C. Relative Humidity: 75% | |
|---|---|---|---|---|
| | Property | Weight change | Property | Weight change |
| Sample 1 (Invention) | white crystalline powder | −0.1% | white crystalline powder | −0.2% |
| Sample 2 (Comparative) | deliquescent | 17.7% | deliquescent | 13.6% |

While the invention has been described in detail and with reference to specific examples thereof, it will be apparent to one skilled in the art that various changes and modifications can be made therein without departing from the spirit and scope thereof.

What is claimed is:

1. Diadenosine tetraphosphate tetrasodium salt dodecahydrate crystals represented by the following structure:

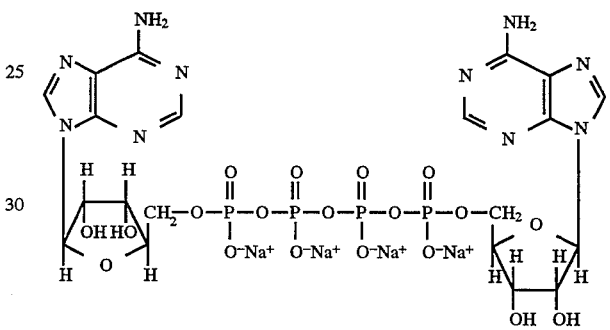

.12 H₂O.

2. The diadenosine tetraphosphate tetrasodium salt dodecahydrate crystals according to claim 1, wherein the water content of the diadenosine tetraphosphate tetrasodium salt dodecahydrate crystals is at least 19.0%.

3. The diadenosine tetraphosphate tetrasodium salt dodecahydrate crystals according to claim 1, wherein the hygroscopicity is in the range of 0 to 3%.

4. A process for preparing the diadenosine tetraphosphate tetrasodium salt dodecahydrate crystals according to claim 1, comprising the steps of:

preparing an amorphous anhydride diadenosine tetraphosphate tetrasodium salt;

purifying the amorphous anhydride diadenosine tetraphosphate tetrasodium salt;

adding a hydrophilic organic solvent to an aqueous solution of the purified amorphous anhydride diadenosine tetraphosphate tetrasodium salt; and precipitating the diadenosine tetraphosphate tetrasodium salt dodecahydrate crystals therefrom.

5. The process according to claim 4, wherein the water content of the diadenosine tetraphosphate tetrasodium salt dodecahydrate crystals is at least 19.0%.

6. The process according to claim 4, wherein the hydrophilic organic solvent is selected from the group consisting of an alcohol, acetone, dioxane and acetonitrile.

7. The process according to claim 4, wherein the hydrophilic organic solvent is an alcohol selected from the group consisting of methanol, ethanol and propanol.

8. The process according to claim 7, wherein the hydrophilic organic solvent is ethanol.

9. The process according to claim 4, wherein the concentration of the hydrophilic organic solvent is not more than 70%.

10. The process according to claim 9, wherein the concentration of the hydrophilic organic solvent is from 20 to 60%.

11. The process according to claim 10, wherein the concentration of the hydrophilic organic solvent is from 30 to 50%.

* * * * *